US011160275B2

(12) United States Patent
Reddy et al.

(10) Patent No.: US 11,160,275 B2
(45) Date of Patent: Nov. 2, 2021

(54) METHODS OF IMPROVING STRESS TOLERANCE, GROWTH AND YIELD IN CEREAL GRAIN CROPS

(71) Applicant: Valent BioSciences LLC, Libertyville, IL (US)

(72) Inventors: Srirama Krishna Reddy, Libertyville, IL (US); Kimberly A. Falco, Crystal Lake, IL (US); Franklin Paul Silverman, Highland Park, IL (US); Marci A. Surpin, Highland Park, IL (US); Dale O. Wilson, Round Lake Beach, IL (US); Derek D. Woolard, Zion, IL (US)

(73) Assignee: VALENT BIOSCIENCES LLC, Libertyville, IL (US)

( * ) Notice: Subject to any disclaimer, the term of this patent is extended or adjusted under 35 U.S.C. 154(b) by 0 days.

(21) Appl. No.: 17/038,460

(22) Filed: Sep. 30, 2020

(65) Prior Publication Data

US 2021/0015095 A1    Jan. 21, 2021

Related U.S. Application Data

(63) Continuation-in-part of application No. 16/135,183, filed on Sep. 19, 2018, now Pat. No. 10,806,097.

(60) Provisional application No. 62/561,292, filed on Sep. 21, 2017, provisional application No. 62/591,379, filed on Nov. 28, 2017.

(51) Int. Cl.
*A01N 37/00* (2006.01)
*A01N 37/02* (2006.01)
*A01N 49/00* (2006.01)

(52) U.S. Cl.
CPC .............. *A01N 37/02* (2013.01); *A01N 49/00* (2013.01)

(58) Field of Classification Search
CPC ........ A01N 37/02; A01N 37/42; A01N 49/00; A01N 45/00; A01N 25/00; A01N 43/12; A01N 37/36; A01H 3/04
See application file for complete search history.

(56) References Cited

U.S. PATENT DOCUMENTS

2006/0084573 A1* 4/2006 Grech ................... C05B 17/00
504/101

FOREIGN PATENT DOCUMENTS

CN          106542912 A  *  3/2017

OTHER PUBLICATIONS

Guo et al. Exogenous malic acid alleviates cadmium toxicity in Miscanthus sacchariflorus through enhancing photosynthetic capacity and restraining ROS accumulation. Ecotoxicology and Environmental Safety 141 (2017) 119-128 (Year: 2017).*
Prijambada et al. Effect of Organic Acids Amendment on the Growth and Yield of Soybean (Glycine max) in Ultisol. Int. J. Agric. Biol., (2010) 12: 566-570. (Year: 2010).*
Travaglia et al. Exogenous ABA Increases Yield in Field-Grown Wheat with Moderate Water Retention. J Plant Growth Regul (2010) 29: 366-374. (Year: 2010).*
Zhang et al. Effects of Plant Growth Regulators on Water Deficit-Induced Yield Loss in Soybean. Proceedings of the 4th International Crop Science Congress (2004) (Year: 2004).*
Espacenet translation for CN106542912 4 pp. (Year: 2021).*

* cited by examiner

*Primary Examiner* — June Hwu
(74) *Attorney, Agent, or Firm* — Wood, Phillips, Katz, Clark & Mortimer

(57) ABSTRACT

The present invention is directed to methods of improving yield in cereal grain crops by applying an effective amount of a mixture of abscisic acid and malic acid to the cereal grain crop. The present invention is further directed to methods of improving growth in cereal grain crops by applying an effective amount of a mixture of abscisic acid and malic acid to the cereal grain crop.

3 Claims, No Drawings

METHODS OF IMPROVING STRESS TOLERANCE, GROWTH AND YIELD IN CEREAL GRAIN CROPS

FIELD OF THE INVENTION

The present invention relates to methods of improving stress tolerance and yield in plants by applying an effective amount of a mixture of (S)-abscisic acid and malic acid to the plant. The present invention further relates to methods of improving growth in plants by applying an effective amount of a mixture of (S)-abscisic acid and malic acid to the plant.

BACKGROUND OF THE INVENTION

Growers continually attempt to grow the most productive crops possible in order to maximize yields. Plant growth regulators are among the best tools that growers can use to influence the growth of plants based on the restrictions of water and temperature. The effects of plant growth regulators on plants under different conditions can vary widely. Furthermore, it is difficult to predict the effect of simultaneously applying more than one plant growth regulator to the plant.

(S)-abscisic acid ("ABA") is an endogenous plant growth regulator with many roles in growth and development. For example, ABA inhibits seed germination by antagonizing gibberellins that stimulate the germination of seeds. ABA promotes stress tolerance and maintains growth under stress conditions (see Sharp R E et al. *J Exp Bot,* 2004 55:2343-2351). Interestingly, several studies have shown that maintaining 'normal' ABA levels in well-watered plants is required to maintain shoot growth in tomato (Sharp R E et al., *J Exp Bot,* 2000 51:1575-1584) and *Arabidopsis thaliana* (LeNoble M E et al. *J Exp Bot,* 2004 55:237-245). Moreover, ABA is responsible for the development and maintenance of dormancy in seeds and woody plants, which when deficient in ABA often demonstrate pre-harvest sprouting of seeds due to a lack of dormancy induction.

Further, applications of ABA have also been shown to provide protection from chilling and drought, as well as to increase the red color of seedless table grapes. Examples of effective commercially available ABA formulations include ProTone™ and Contego™ (available from Valent BioSciences LLC).

Malic acid is an intermediate compound in the citric acid (TCA) cycle, and the C4 carbon fixation process of the chloroplast. In addition, malic acid is synthesized by stomatal guard cells in plant leaves and has been shown to play an important role in stomatal control; however, it is unclear whether malic acid promotes opening or closure of the stomates (Araujo W L et al., Control of stomatal aperture, *Plant Signal Behav.* 2011 September, 6(9), 1305-1311) as there are evidences supporting each hypothesis.

Exogenous malic acid may promote plant growth (Talebi et al., *Adv in Agri,* 2014, 147: 278). Malic acid application resulted in increased photosynthesis under cadmium stress (Guo et al., *Ecotoxicology and Environmental Safety,* 141 (2017), 119-128). Thus, although malic acid has an effect on growth and transpiration in plants; it is unclear how exogenous malic acid effects plant growth under water deficit stress conditions, especially in combination with ABA, a known stress tolerance compound.

Accordingly, there is a need in the art for new methods to improve the growth of plants under abiotic stress conditions.

SUMMARY OF THE INVENTION

In one aspect, the present invention is directed to methods of improving stress tolerance in a plant comprising applying an effective amount of (S)-abscisic acid ("ABA") and malic acid to the plant, wherein the weight ratio of ABA to malic acid is from about 3.3:1 to about 1:30.

In another aspect, the present invention is directed to methods of improving yield in a plant comprising applying an effective amount of (S)-abscisic acid ("ABA") and malic acid to the plant, wherein the weight ratio of ABA to malic acid is from about 3.3:1 to about 1:33.3.

In another aspect, the present invention is directed to methods of improving plant growth comprising applying an effective amount of (S)-abscisic acid ("ABA") and malic acid to the plant, wherein the weight ratio of ABA to malic acid is from about 3.3:1 to about 1:30.

DETAILED DESCRIPTION OF THE INVENTION

Applicant unexpectedly discovered a mixture of (S)-abscisic acid ("ABA") and malic acid improved drought stress tolerance and plant growth under stress conditions. Applicant further discovered that a mixture of ABA and malic acid unexpectedly improved plant growth under normal conditions. Further, the Applicant discovered that a mixture of ABA and malic acid unexpectedly improved water use efficacy as demonstrated by unexpected increase in water banking (i.e. storing of water for future use). Applicant also discovered that a mixture of ABA and malic acid unexpectedly increased carbon fixing as demonstrated by an unexpected increase in photosynthetic rate and dry weight.

In one embodiment, the present invention is directed to methods of improving plant growth comprising applying an effective amount of ABA and malic acid to the plant, wherein the weight ratio of ABA to malic acid is from about 3.3:1 to about 1:33.3.

In another preferred embodiment, the plant in which plant growth is improved is subject to an abiotic stress.

In another embodiment, the present invention is directed to methods of improving stress tolerance in a plant comprising applying an effective amount of ABA and malic acid to the plant, wherein the weight ratio of ABA to malic acid is from about 3.3:1 to about 1:30.

In a preferred embodiment, the stress tolerance that is improved is an abiotic stress.

In a preferred embodiment, ABA and malic acid are applied at a weight ratio from about 10:1 to about 1:33.3, from about 10:1 to about 1:30:1, from about 3.3:1 to about 1:30, from about 3.3:1 to about 1:10, from about 3.3:1 to about 1:3.3, from about 3:1 to about 1:3, from about 1:3 to about 1:33.3, from about 1:3 to about 1:30, from about 1:3 to about 1:10, from about 3.3:1 to about 3:1 or about 3.3:1, 3:1, 1:1, 1:3, 1:3.3, 1:10, 1:30 or 1:33.3.

In another embodiment, the plant is a monocotyledonous plant or a dicotyledonous plant. In a preferred embodiment the plant is selected from the group consisting of root, corm and tuber vegetable plants, bulb vegetable plants, leafy non-brassica vegetable plants, leafy brassica vegetable plants, succulent or dried legume plants, fruiting vegetable plants, cucurbit vegetable plants, citrus fruit plants, pome fruit plants, stone fruit plants, berry and small fruit plants, tree nut plants, cereal crops, forage and fodder grasses and hay, non-grass animal feed plants, herb plants, spice plants, flower plants, bedding plants, ornamental flower plants, artichoke, asparagus, tropical fruit plants, hops, malanga, peanut, pomegranate plants, oil seed vegetable plants, tobacco plants, turf grass and watercress plant. In a more preferred embodiment, the plant is wheat, corn, rice or lettuce.

In a preferred embodiment, the root, corm and tuber vegetable plants are selected from the group consisting of arracacha, arrowroot, Chinese artichoke, Jerusalem artichoke, garden beet, sugar beet, edible burdock, edible canna, carrot, bitter cassava, sweet cassava, celeriac, root chayote, turnip-rooted chervil, chicory, chufa, dasheen (taro), ginger, ginseng, horseradish, leren, turnip-rooted parsley, parsnip, potato, radish, oriental radish, rutabaga, salsify, black salsify, Spanish salsify, skirret, sweet potato, tanier, turmeric, turnip, yam bean, true yam, and cultivars, varieties and hybrids thereof.

In another preferred embodiment, the bulb vegetable plants are selected from the group consisting of fresh chive leaves, fresh Chinese chive leaves, bulb daylily, elegans hosta, bulb fritillaria, fritillaria leaves, bulb garlic, great-headed bulb garlic, serpent bulb garlic, kurrat, lady's leek, leek, wild leek, bulb lily, Beltsville bunching onion, bulb onion, Chinese bulb onion, fresh onion, green onion, macrostem onion, pearl onion, potato bulb onion, potato bulb, tree onion tops, Welsh onion tops, bulb shallot, fresh shallot leaves, and cultivars, varieties and hybrids thereof.

In a further embodiment, the leafy non-brassica vegetable plants are selected from the group consisting of Chinese spinach Amaranth, leafy Amaranth, arugula (roquette), cardoon, celery, Chinese celery, celtuce, chervil, Chinese spinach, edible-leaved chrysanthemum, garland chrysanthemum, corn salad, garden cress, upland cress, dandelion, dandelion leaves, sorrels (dock), endive (escarole), Florence fennel, head lettuce, leaf lettuce, orach, parsley, garden purslane, winter purslane, radicchio (red chicory), rhubarb, spinach, New Zealand spinach, vine spinach, Swiss chard, Tampala, and cultivars, varieties and hybrids thereof.

In another embodiment, the leafy brassica vegetable plants are selected from the group consisting of broccoli, Chinese broccoli (gai lon), broccoli rabe (rapini), Brussels sprouts, cabbage, Chinese cabbage (bok choy), Chinese napa cabbage, Chinese mustard cabbage (gai choy), cauliflower, cavolo broccoli, collards, kale, kohlrabi, mizuna, mustard greens, mustard spinach, rape greens, turnip greens and cultivars, varieties and hybrids thereof. In yet another embodiment, the succulent or dried vegetable legumes are selected from the group consisting of *Lupinus* beans, *Phaseolus* beans, *Vigna* beans, broad beans (fava), chickpea (garbanzo), guar, jackbean, lablab bean, lentil, *Pisum* peas, pigeon pea, soybean, immature seed soybean, sword bean, peanut, and cultivars, varieties and hybrids thereof. In a preferred embodiment, the *Lupinus* beans include grain lupin, sweet lupin, white lupin, white sweet lupin, and hybrids thereof. In another preferred embodiment, the *Phaseolus* beans include field bean, kidney bean, lima bean, navy bean, pinto bean, runner bean, snap bean, tepary bean, wax bean, and hybrids thereof. In yet another preferred embodiment, the *Vigna* beans include adzuki bean, asparagus bean, blackeyed bean, catjang, Chinese longbean, cowpea, Crowder pea, moth bean, mung bean, rice bean, southern pea, urd bean, yardlong bean, and hybrids thereof. In another embodiment, the *Pisum* peas include dwarf pea, edible-podded pea, English pea, field pea, garden pea, green pea, snow pea, sugar snap pea, and hybrids thereof. In a preferred embodiment, the dried vegetable legume is soybean. In a more preferred embodiment, the dried vegetable legume is genetically modified soybean.

In a further embodiment, the fruiting vegetable plants are selected from the group consisting of bush tomato, cocona, currant tomato, garden huckleberry, goji berry, groundcherry, martynia, naranjilla, okra, pea eggplant, pepino, bell peppers, non-bell peppers, roselle, eggplant, scarlet eggplant, African eggplant, sunberry, tomatillo, tomato, tree tomato, and cultivars, varieties and hybrids thereof. In a preferred embodiment, the peppers include bell peppers, chili pepper, cooking pepper, pimento, sweet peppers, and hybrids thereof.

In an embodiment, the cucurbit vegetable plants are selected from the group consisting of Chayote, Chayote fruit, waxgourd (Chinese preserving melon), citron melon, cucumber, gherkin, edible gourds, *Momordica* species, muskmelons, pumpkins, summer squashes, winter squashes, watermelon, and cultivars, varieties and hybrids thereof. In a preferred embodiment, edible gourds include hyotan, cucuzza, hechima, Chinese okra, and hybrids thereof. In another preferred embodiment, the *Momordica* vegetables include balsam apple, balsam pear, bittermelon, Chinese cucumber, and hybrids thereof. In another preferred embodiment, the muskmelon include true cantaloupe, cantaloupe, casaba, crenshaw melon, golden pershaw melon, honeydew melon, honey balls, mango melon, Persian melon, pineapple melon, Santa Claus melon, snake melon, and hybrids thereof. In yet another preferred embodiment, the summer squash include crookneck squash, scallop squash, straight-neck squash, vegetable marrow, zucchini, and hybrids thereof. In a further preferred embodiment, the winter squash includes butternut squash, calabaza, hubbard squash, acorn squash, spaghetti squash, and hybrids thereof.

In another embodiment, the citrus fruit plants are selected from the group consisting of limes, calamondin, citron, grapefruit, Japanese summer grapefruit, kumquat, lemons, Mediterranean mandarin, sour orange, sweet orange, pummelo, Satsuma mandarin, tachibana orange, tangelo, mandarin tangerine, tangor, trifoliate orange, uniq fruit, and cultivars, varieties and hybrids thereof. In a preferred embodiment, the limes are selected from the group consisting of Australian desert lime, Australian finger lime, Australian round lime, Brown River finger lime, mount white lime, New Guinea wild lime, sweet lime, Russell River lime, Tahiti lime, and hybrids thereof.

In an embodiment, the pome fruit plants are selected from the group consisting of apple, azarole, crabapple, loquat, mayhaw, medlar, pear, Asian pear, quince, Chinese quince, Japanese quince, tejocote, and cultivars, varieties and hybrids thereof.

In another embodiment, the stone fruit plants are selected from the group consisting of apricot, sweet cherry, tart cherry, nectarine, peach, plum, Chicksaw plum, Damson plum, Japanese plum, plumcot, fresh prune, and cultivars, varieties and hybrids thereof.

In a further embodiment, the berries and small fruit plants are selected from the group consisting of Amur river grape, aronia berry, bayberry, bearberry, bilberry, blackberry, blueberry, lowbush blueberry, highbush blueberry, buffalo currant, buffaloberry, che, Chilean guava, chokecherry, cloudberry, cranberry, highbush cranberry, black currant, red currant, elderberry, European barberry, gooseberry, grape, edible honeysuckle, huckleberry, jostaberry, Juneberry (Saskatoon berry), lingonberry, maypop, mountain pepper berries, mulberry, muntries, native currant, partridgeberry, phalsa, pincherry, black raspberry, red raspberry, riberry, salal, sea buckthorn, serviceberry, strawberry, wild raspberry, and cultivars, varieties and hybrids thereof. In a preferred embodiment, the blackberries include Andean blackberry, arctic blackberry, bingleberry, black satin berry, boysenberry, brombeere, California blackberry, Chesterberry, Cherokee blackberry, Cheyenne blackberry, common blackberry, coryberry, darrowberry, dewberry, Dirksen thornless berry, evergreen blackberry, Himalayaberry, hullberry, lavacaberry, loganberry, lowberry, Lucreliaberry, mammoth blackberry, marionberry, mora, mures deronce, nectarberry, Northern dewberry, olallieberry, Oregon evergreen berry, phenomenalberry, rangeberry, ravenberry, rossberry, Shawnee blackberry, Southern dewberry, tayberry, youngberry, zarzamora, and hybrids thereof.

In another embodiment, the tree nut plants are selected from the group consisting of almond, beech nut, Brazil nut, Brazilian pine, bunya, butternut, bur oak, Cajou nut, candlenut, cashew, chestnut, chinquapin, coconut, coquito nut, dika nut, gingko, Guiana chestnut, hazelnut (filbert), heartnut, hickory nut, Japanese horse-chestnut, macadamia nut, mongongo nut, monkey-pot, monkey puzzule nut, Okari nut, Pachira nut, peach palm nut, pecan, Pili nut, pistachio, Sapucaia nut, tropical almond, black walnut, English walnut, yellowhorn, and cultivars, varieties and hybrids thereof.

In a further embodiment, the cereal grains are selected from the group consisting of barley, buckwheat, pearl millet, proso millet, oats, corn, field corn, sweet corn, seed corn, popcorn, rice, rye, sorghum (milo), sorghum species, grain sorghum, sudangrass (seed), teosinte, triticale, wheat, wild rice, and cultivars, varieties and hybrids thereof. In a preferred embodiment, the cereal grain is selected from the group consisting of wheat, rice and corn. In a more preferred embodiment, the cereal grain is genetically modified corn.

In yet another embodiment, the grass forage, fodder and hay are selected from the group consisting of grasses that are members of the Gramineae family except sugarcane and those species included in the cereal grains group, pasture and range grasses, and grasses grown for hay or silage. In further embodiments, the Gramineae grasses may be green or cured.

In an embodiment, the non-grass animal feeds are selected from the group consisting of alfalfa, velvet bean, trifolium clover, melilotus clover, kudzu, lespedeza, lupin, sainfoin, trefoil, vetch, crown vetch, milk vetch, and cultivars, varieties and hybrids thereof.

In another embodiment, the herbs and spice plants are selected from the group consisting of allspice, angelica, anise, anise seed, star anise, annatto seed, balm, basil, borage, burnet, chamomile, caper buds, caraway, black caraway, cardamom, cassia bark, cassia buds, catnip, celery seed, chervil, chive, Chinese chive, cinnamon, clary, clove buds, coriander leaf, coriander seed, costmary, culantro leaves, culantro seed, cilantro leaves, cilantro seed, cumin, dillweed, dill seed, fennel, common fennel, Florence fennel seed, fenugreek, grains of paradise, horehound, hyssop, juniper berry, lavender, lemongrass, leaf lovage, seed lovage, mace, marigold, marjoram, mint, mustard seed, nasturtium, nutmeg, parsley, pennyroyal, black pepper, white pepper, poppy seed, rosemary, rue, saffron, sage, summer savory, winter savory, sweet bay, tansy, tarragon, thyme, vanilla, wintergreen, woodruff, wormwood, and cultivars, varieties and hybrids thereof. In a preferred embodiment, the mints are selected from the group consisting of spearmint, peppermint, and hybrids thereof.

In yet another embodiment, artichokes are selected from the group consisting of Chinese artichoke, Jerusalem artichoke, and cultivars, varieties and hybrids thereof.

In an embodiment, the tropical fruit plants are selected from the group consisting of anonna, avocado, fuzzy kiwifruit, hardy kiwifruit, banana, plantain, caimito, carambola (star fruit), guava, longan, sapodilla, papaya, passion fruit, mango, lychee, jackfruit, dragon fruit, mamey sapote, coconut cherimoya, canistrel, monstera, wax jambu, pomegranate, rambutan, pulasan, Pakistani mulberry, langsat, chempedak, durian, fig pineapple, jaboticaba, mountain apples, and cultivars, varieties and hybrids thereof.

In a further embodiment, the oil seed vegetable plants are selected from the group consisting of borage, calendula, castor oil plant, tallowtree, cottonseed, crambe, cuphea, echium, euphorbia, evening primrose, flax seed, gold of pleasure, hare's ear, mustard, jojoba, lesquerella, lunaria, meadowfoam, milkweed, niger seed, oil radish, poppy seed, rosehip, sesame, stokes aster, sweet rocket, tallowwood, tea oil plant, vermonia, canola, or oil rapeseed, safflower, sunflower, and cultivars, varieties and hybrids thereof.

In another embodiment, the plant is subjected to drought stress. As used herein, "drought stress" refers to watering conditions wherein plant growth is significantly slowed as compared to those where water availability is sufficient to support optimal growth and development.

In a preferred embodiment, ABA and malic acid is applied prior to or during the advent of abiotic stress. When the intended stress is drought, application of ABA and malic acid occurs prior to or during drought stress. Application prior to drought allows for banking of soil water. By conserving soil water plants can extend survival and growth during critical growth stages, when yield losses due to water stress are higher.

In another preferred embodiment, from about 1 to 1,000 parts per million ("ppm") of ABA are applied to the plant, more preferably from about 30 to 1,000 ppm or from 30 to 300 ppm.

In another preferred embodiment, from about 1 to 1,000 parts per million ("ppm") of malic acid are applied to the plant, more preferably from about 30 to 1,000 ppm or from 30 to 300 ppm.

In another preferred embodiment, ABA is applied to the plant at a rate from about 1 to about 1,000 liters per hectare ("L/Ha"), more preferably from about 10 to about 500 L/Ha and most preferably from about 100 to about 200 L/Ha.

In another preferred embodiment, malic acid is applied to the plant at a rate from about 1 to about 1,000 L/Ha, more preferably from about 10 to about 500 L/Ha and most preferably from about 100 to about 200 L/Ha.

The ABA and malic acid mixture can be applied by any convenient means. Those skilled in the art are familiar with the modes of application that include foliar applications such as spraying, dusting, and granular applications; soil applications including spraying, in-furrow treatments, or side-dressing.

In another preferred embodiment, the present invention is directed to a composition comprising ABA and malic acid, wherein the weight ratio of ABA to malic acid is from about 10:1 to about 1:33.3, from about 10:1 to about 1:30:1, from about 3.3:1 to about 1:30, from about 3.3:1 to about 1:10, from about 3.3:1 to about 1:3.3, from about 3:1 to about 1:3, from about 1:3 to about 1:33.3, from about 1:3 to about 1:30, from about 1:3 to about 1:10, from about 3.3:1 to about 3:1 or about 3.3:1, 3:1, 1:1, 1:3, 1:3.3, 1:10, 1:30 or 1:33.3.

Aqueous spray solutions utilized in the present invention generally contain from about 0.01% to about 0.5% (v/v) of a non-ionic surface-active agent.

The surface-active agent comprises at least one non-ionic surfactant. In general, the non-ionic surfactant may be any known non-ionic surfactant in the art. Suitable non-ionic surfactants are in general oligomers and polymers. Suitable polymers include alkyleneoxide random and block copolymers such as ethylene oxide-propylene oxide block copolymers (EO/PO block copolymers), including both EO-PO-EO and PO-EO-PO block copolymers; ethylene oxide-butylene oxide random and block copolymers, C2-6 alkyl adducts of ethylene oxide-propylene oxide random and block copolymers, C2-6 alkyl adducts of ethylene oxide-butylene oxide random and block copolymers, polyoxyethylene-polyoxypropylene monoalkylethers, such as methyl ether, ethyl ether, propyl ether, butyl ether or mixtures thereof; vinylacetate/vinylpyrrolidone copolymers; alkylated vinylpyrrolidone copolymers; polyvinylpyrrolidone; and polyalkyleneglycol, including the polypropylene glycols and polyethylene glycols. Other non-ionic agents are the lecithins; and silicone surface active agents (water soluble or dispersible surface-active agents having a skeleton which comprises a siloxane chain e.g. Silwet L77®). A suitable mixture in mineral oil is ATPLUS® 411.

As used herein, "effective amount" refers to the amount of the ABA and/or malic acid that will improve growth, drought stress tolerance, and/or yield. The "effective amount" will vary depending on the ABA and malic acid concentrations, the plant species or variety being treated, the severity of the stress, the result desired, and the life stage of the plants, among other factors. Thus, it is not always possible to specify an exact "effective amount." However, an appropriate "effective amount" in any individual case may be determined by one of ordinary skill in the art.

As used herein, "improving" means that the plant has more of the quality than the plant would have had it if it had not been treated by methods of the present invention.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

The articles "a," "an" and "the" are intended to include the plural as well as the singular, unless the context clearly indicates otherwise.

The disclosed embodiments are simply exemplary embodiments of the inventive concepts disclosed herein and should not be considered as limiting, unless the claims expressly state otherwise.

The following examples are intended to illustrate the present invention and to teach one of ordinary skill in the art how to use the formulations of the invention. They are not intended to be limiting in any way.

EXAMPLES

Example 1. Increased Stress Tolerance in Cucumber Plants Under Drought Stress 10 sets of cucumber plants (n=5) were each treated on 10 post-planting day ("DAP") with either 30 or 100 ppm ABA, 30 or 100 ppm malic acid or mixtures thereof. Water was withheld starting on 10 DAP for 5 sets and the other sets were fully irrigated. Green leaf area was measured using a handheld Greenseeker® crop sensor, which uses a normalized difference vegetative index ("NDVI") to measure green leaf area. Green leaf area was measured and recorded everyday starting on 10 DAP and ending on day 4 post-treatment ("DAT"). Results of these measurement can be seen in Table 1, below.

To determine if the mixtures provided unexpected results, the observed combined efficacy ("OCE") was divided by the expected combined efficacy ("ECE") to give an OCE/ECE ratio wherein the expected ECE is calculated by the Abbott method:

$$ECE = A + B - (AB/100),$$

wherein ECE is the expected combined efficacy and in which A and B are the efficacy provided by the single active ingredients. If the ratio between the OCE of the mixture and the ECE of the mixture is greater than 1, then greater than expected interactions are present in the mixture. (Gisi, *The American Phytopathological Society*, 86:11, 1273-1279, 1996).

TABLE 1

|  | NDVI | % Change from STC | OCE/ECE ratio |
|---|---|---|---|
| STC | 0.595 | n/a | n/a |
| ABA 100 ppm | 0.72 | 21.0% | n/a |
| Malic acid 30 ppm | 0.563 | −5.4% | n/a |
| ABA 100 ppm + Malic acid 30 ppm | 0.944 | 58.7% | 1.4 |
| ABA 100 ppm + Malic acid 100 ppm | 0.956 | 60.7% | n/a |

"STC" denotes surfactant treated control

As seen in Table 1, ABA increased green leaf area whereas malic acid decreased green leaf area. A mixture of ABA and malic acid at a ratio of 3.3:1 demonstrated an unexpected increase in green leaf area.

Example 2. Increased Stress Tolerance in Cucumber Plants Under Drought Stress 11 sets of cucumber plants (n=8) were each treated on day 10 DAP with either 30 or 100 ppm ABA, 30 or 100 ppm malic acid or mixtures thereof. Water was withheld starting on 10 DAP. Green leaf area was measured and recorded everyday starting on 10 DAP and ending on day 4 post-treatment ("DAT"). Results of these measurement can be seen in Table 2, below.

TABLE 2

|  | NDVI | % Change from UTC | OCE/ECE ratio |
|---|---|---|---|
| STC | 1.58 | 0% | n/a |
| ABA 30 ppm | 1.32 | −16.5% | n/a |
| ABA 100 ppm | 1.78 | 12.7% | n/a |
| Malic acid 30 ppm | 1.78 | 12.7% | n/a |
| Malic acid 100 ppm | 1.36 | −13.9% | n/a |
| ABA 30 ppm + Malic acid 30 ppm | 2.07 | 31.0% | 1.4 |
| ABA 30 ppm + Malic acid 100 ppm | 2.23 | 41.1% | 2.0 |
| ABA 100 ppm + Malic acid 30 ppm | 2.02 | 27.8% | 1.0 |
| ABA 100 ppm + Malic acid 100 ppm | 2.14 | 35.4% | 1.4 |

"STC" denotes surfactant treated control

As seen in Table 2, ABA and malic acid each increased and decreased green leaf area depending on concentration. Unexpectedly, a mixture of ABA and malic acid at ratios of 1:1, 1:3.3, 3.3:1 provided greater than expected increase in green leaf area when plants were subjected to water deficit stress.

Example 3. Increased Dry Weight in Cucumber Plants Under Drought Stress 6 sets of cucumber plants (n=5) were each treated on 10 DAP with either 100 ppm ABA, 30, 100 or 300 ppm malic acid or mixtures thereof. Water was withheld from 10 DAP to 4 DAT. Water was applied on 4 DAT. Water was withheld from 5 DAT to 7 DAT. Plants were harvested, and dry weight was measured and recorded on 7 DAT. This experiment was repeated with harvest occurring 8 DAT. Results of these measurements can be seen in Tables 3 and 4, below, respectively.

TABLE 3

|  | Increase in Dry Weight | % Change from UTC | OCE/ECE ratio (Linear) |
|---|---|---|---|
| STC | 0.99 | n/a | n/a |
| ABA 100 ppm | 1.04 | 5.1% | n/a |
| Malic acid 30 ppm | 1.01 | 2.0% | n/a |
| ABA 100 ppm + Malic acid 30 ppm | 1.24 | 25.3% | 1.2 |
| ABA 100 ppm + Malic acid 100 ppm | 1.36 | 37.4% | n/a |
| ABA 100 ppm + Malic acid 300 ppm | 1.13 | 14.1% | n/a |

"STC" denotes—surfactant treated control

TABLE 4

| Treatment | Increase in Dry Weight | % Change from UTC | OCE/ECE ratio |
|---|---|---|---|
| STC | 0.98 | 0.0% | n/a |
| ABA 100 ppm | 0.96 | -2.2% | n/a |
| Malic acid 30 ppm | 1.14 | 15.9% | n/a |
| ABA 100 ppm + Malic acid 30 ppm | 1.27 | 30.0% | 1.1 |
| ABA 100 ppm + Malic acid 100 ppm | 1.04 | 6.1% | n/a |
| ABA 100 ppm + Malic acid 300 ppm | 0.97 | -1.4% | n/a |

"STC" denotes—surfactant treated control

As seen in Table 3 and 4, mixtures of ABA and malic acid improved dry weight over the control and over the application of either alone at all concentrations. The mixtures of ABA and malic acid at a 3.3:1 ratio demonstrated unexpected increase in dry weight.

Example 4. Increased Water Banking in Wheat Plants Under Drought Stress 8 sets of wheat plants (n=8) were each treated 1 week after anthesis with either 300 ppm ABA, 1000 ppm malic acid or a mixture thereof. Water was withheld for three days after treatment and kept well-watered for next four days. Chemical spray treatment was repeated one week after the initial spray followed by similar drought cycle and irrigation. This experiment was then repeated. Evapotranspiration (i.e. change in pot weight) was measured on 1, 2 and 3 DAT for each cycle. Results showing unexpected increase in water banking via application of ABA and malic acid can be seen for the $2^{nd}$ cycle of the $1^{st}$ experiment and for the $1^{st}$ and $2^{nd}$ cycles of the $2^{nd}$ experiment in Tables 5-7, below.

TABLE 5

| Experiment #1 | Evapotranspiration | | | % Change from UTC | | | OCE/ECE ratio | | |
|---|---|---|---|---|---|---|---|---|---|
| ($2^{nd}$ Cycle) | 1 DAT | 2 DAT | 3 DAT | 1 DAT | 2 DAT | 3 DAT | 1 DAT | 2 DAT | 3 DAT |
| STC | 70.18 | 83.62 | 22.46 | 0 | 0 | 0 | n/a | n/a | n/a |
| ABA 300 ppm | 46.62 | 83.36 | 34.73 | -33.6% | -0.3% | 54.6% | n/a | n/a | n/a |
| Malic acid 1000 ppm | 74.37 | 82.09 | 22.72 | 6.0% | -1.8% | 1.2% | n/a | n/a | n/a |
| ABA 300 ppm + Malic acid 1000 ppm | 50.04 | 74.45 | 40.59 | -28.7% | -11.0% | 80.7% | 1.0 | 0.9 | 1.2 |

TABLE 6

| Experiment #2 | Evapotranspiration | | | % Change from UTC | | | OCE/ECE ratio | | |
|---|---|---|---|---|---|---|---|---|---|
| ($1^{st}$ Cycle) | 1 DAT | 2 DAT | 3 DAT | 1 DAT | 2 DAT | 3 DAT | 1 DAT | 2 DAT | 3 DAT |
| STC | 111.15 | 61.76 | 18.17 | 0.0% | 0.0% | 0.0% | n/a | n/a | n/a |
| ABA 300 ppm | 61.61 | 67.91 | 44.98 | -44.6% | 10.0% | 147.6% | n/a | n/a | n/a |
| Malic acid 1000 ppm | 102.06 | 67.83 | 18.18 | -8.2% | 9.8% | 0.1% | n/a | n/a | n/a |
| ABA 300 ppm + Malic acid 1000 ppm | 55.2 | 67.42 | 51.26 | -50.3% | 9.2% | 182.1% | 1.1 | 0.9 | 1.1 |

TABLE 7

| Experiment #2 | Evapotranspiration | | | % Change from UTC | | | OCE/ECE ratio | | |
|---|---|---|---|---|---|---|---|---|---|
| ($2^{nd}$ Cycle) | 1 DAT | 2 DAT | 3 DAT | 1 DAT | 2 DAT | 3 DAT | 1 DAT | 2 DAT | 3 DAT |
| STC | 50.81 | 60.12 | 43.2 | 0.0% | 0.0% | 0.0% | n/a | n/a | n/a |
| ABA 300 ppm | 57.27 | 71.83 | 46.86 | 12.7% | 19.5% | 8.5% | n/a | n/a | n/a |
| Malic acid 1000 ppm | 51.41 | 62.73 | 46.17 | 1.2% | 4.3% | 6.9% | n/a | n/a | n/a |
| ABA 300 ppm + Malic acid 1000 ppm | 50.41 | 65.81 | 57.85 | -0.8% | 9.5% | 33.9% | 0.9 | 0.9 | 1.2 |

"STC" Denotes Untreated Control

As seen in Tables 5-7, both ABA and malic acid alone demonstrated evidence of water banking. Evidence of water banking can be seen by the greater amounts of evapotranspiration during drought stress, particularly 3 DAT. A mixture of ABA and malic acid at a ratio of 1:3.3 demonstrated unexpected levels of water banking, especially 3 DAT during $1^{st}$ and $2^{nd}$ cycle of drought stress.

Example 5. Increased Water Banking in Wheat Plants Under Drought Stress 10 sets of wheat plants (n=6) were each treated 1 week after anthesis with either 100 or 300 ppm ABA, 100, 300 or 1000 ppm malic acid or mixtures thereof in a 0.025% Latron B 1956® (available from J.R. Simplot Company) surfactant solution. Water was withheld from the day of chemical treatment. Evapotranspiration was measured on 1, 2 and 3 DAT as the amount of water left in the pot compared to day 0. Results can be seen in Table 8, below.

TABLE 8

|  | Evapotranspiration | | | % Change from STC | | | OCE/ECE ratio | | |
| --- | --- | --- | --- | --- | --- | --- | --- | --- | --- |
|  | 1 DAT | 2 DAT | 3 DAT | 1 DAT | 2 DAT | 3 DAT | 1 DAT | 2 DAT | 3 DAT |
| STC | 0.763 | 0.404 | 0.257 | 0.0% | 0.0% | 0.0% | n/a | n/a | n/a |
| 100 ppm ABA | 0.834 | 0.582 | 0.321 | 9.4% | 44.2% | 24.7% | n/a | n/a | n/a |
| 300 ppm ABA | 0.837 | 0.610 | 0.349 | 9.8% | 51.1% | 35.5% | n/a | n/a | n/a |
| 100 ppm Malic acid | 0.780 | 0.438 | 0.269 | 2.3% | 8.4% | 4.5% | n/a | n/a | n/a |
| 300 ppm Malic acid | 0.751 | 0.404 | 0.260 | −1.5% | −0.1% | 1.1% | n/a | n/a | n/a |
| 1000 ppm Malic acid | 0.736 | 0.390 | 0.251 | −3.4% | −3.4% | −2.4% | n/a | n/a | n/a |
| 100 ppm ABA + 100 ppm Malic acid | 0.854 | 0.617 | 0.344 | 12.0% | 52.9% | 33.6% | 1.0 | 1.0 | 1.0 |
| 100 ppm ABA + 300 ppm Malic acid | 0.850 | 0.620 | 0.346 | 11.5% | 53.7% | 34.4% | 1.0 | 1.1 | 1.1 |
| 100 ppm ABA + 1000 ppm Malic acid | 0.859 | 0.631 | 0.350 | 12.7% | 56.2% | 36.0% | 1.1 | 1.1 | 1.1 |
| 300 ppm ABA + 100 ppm Malic acid | 0.876 | 0.658 | 0.386 | 14.9% | 63.1% | 49.8% | 1.0 | 1.0 | 1.1 |
| 300 ppm ABA + 300 ppm Malic acid | 0.880 | 0.675 | 0.407 | 15.4% | 67.2% | 57.9% | 1.1 | 1.1 | 1.2 |
| 300 ppm ABA + 1000 ppm Malic acid | 0.889 | 0.685 | 0.413 | 16.5% | 69.8% | 60.3% | 1.1 | 1.1 | 1.2 |

"STC" denotes surfactant treated control

As seen in Table 8, both ABA and malic acid alone demonstrated evidence of water banking. Evidence of water banking can be seen by the greater amounts of evapotranspiration during drought stress, particularly 3 DAT. A mixture of ABA and malic acid at a ratio of 3:1, 1:1, 1:3, 1:3.3, and 1:10 demonstrated unexpected levels of water banking, especially 3 DAT as the amount of water left in the pot compared to day 0.

Example 6. Increased Water Banking in Wheat Plants Under Drought Stress

−10 sets of wheat plants (n=6) were each treated 1 week after anthesis with either 100 or 300 ppm ABA, 1000 ppm malic acid or mixtures thereof in a 0.025% Latron B 1956® surfactant solution. Water was withheld during the treatment. Evapotranspiration was measured on 1, 2 and 3 DAT. Results can be seen in Table 9, below.

TABLE 9

|  | Evapotranspiration | | | % Change from STC | | | OCE/ECE ratio | | |
| --- | --- | --- | --- | --- | --- | --- | --- | --- | --- |
|  | 1 DAT | 2 DAT | 3 DAT | 1 DAT | 2 DAT | 3 DAT | 1 DAT | 2 DAT | 3 DAT |
| STC | 0.728 | 0.358 | 0.230 | 7.8% | 42.6% | 15.5% | n/a | n/a | n/a |
| 100 ppm ABA | 0.785 | 0.510 | 0.266 | 9.9% | 56.1% | 26.6% | n/a | n/a | n/a |
| 300 ppm ABA | 0.800 | 0.558 | 0.292 | 0.6% | 3.6% | 3.6% | n/a | n/a | n/a |
| 1000 ppm Malic acid | 0.733 | 0.370 | 0.239 | 16.6% | 78.0% | 63.8% | n/a | n/a | n/a |
| 300 ppm ABA + 1000 ppm Malic acid | 0.848 | 0.636 | 0.378 | 7.8% | 42.6% | 15.5% | 1.1 | 1.1 | 1.3 |

"STC" denotes surfactant treated control

As seen in Table 9, both ABA and malic acid alone demonstrated evidence of water banking. Evidence of water banking can be seen by the greater amounts of evapotranspiration during drought stress, particularly 3 DAT. A mixture of ABA and malic acid at a ratio of 1:3.3 demonstrated unexpected levels of water banking, especially 3 DAT as the amount of water left in the pot compared to day 0.

Example 7. Increased Grain Yield in Wheat Plants Under Drought Stress 8 sets of wheat plants (n=8) were each treated at one week after anthesis with either 300 ppm ABA, 1000 ppm malic acid or a mixture thereof; chemical treatment with same compounds was repeated one week after initial spray. Water was withheld during the treatment. Shoot weight, spike weight and grain yield were measured at physiological maturity. Results can be seen in Table 10, below.

TABLE 10

| | Drought Stress | | | % Change from UTC | | | OCE/ECE ratio | | |
| --- | --- | --- | --- | --- | --- | --- | --- | --- | --- |
| | Shoot Weight | Spike Weight | Grain Weight | Shoot Weight | Spike Weight | Grain Weight | Shoot Weight | Spike Weight | Grain Weight |
| STC | 3.03 | 6.80 | 4.99 | 0.0% | 0.0% | 0.0% | n/a | n/a | n/a |
| ABA 300 ppm | 3.38 | 7.27 | 5.25 | 11.9% | 6.8% | 5.1% | n/a | n/a | n/a |
| Malic acid 1000 ppm | 3.13 | 6.98 | 4.91 | 3.5% | 2.6% | −1.7% | n/a | n/a | n/a |
| ABA 300 ppm + Malic acid 1000 ppm | 3.39 | 7.61 | 5.58 | 11.9% | 11.9% | 11.8% | 1.0 | 1.0 | 1.1 |

"STC" denotes surfactant treated control

As can be seen in Table 10, ABA alone demonstrated evidence of increased grain weight, whereas malic acid alone demonstrated evidence of decreased grain weight. A mixture of ABA and malic acid at a 1:3.3 ratio demonstrated an unexpected increase in grain weight.

Example 8. Increased Weight in Lettuce Under Drought Stress 8 sets of lettuce plants (n=8) were each treated 20 DAP with either 300 ppm ABA, 1000 ppm malic acid or a mixture thereof. Water was withheld during the treatment. Fresh weight and dry weight were measured 34 DAT. Results can be seen in Tables 11 and 12, below.

TABLE 11

| Fresh Weight | Weight (g) | % Change from UTC | OCE/ECE ratio |
| --- | --- | --- | --- |
| UTC | 15.3 | n/a | n/a |
| ABA 300 ppm | 15.9 | 6.7% | n/a |
| Malic acid 1000 ppm | 10.8 | −26.7% | n/a |
| ABA 300 ppm + Malic acid 1000 ppm | 17.8 | 16.7% | 1.5 |

TABLE 12

| Dry Weight | Weight (g) | % Change from UTC | OCE/ECE ratio |
| --- | --- | --- | --- |
| UTC | 1.88 | n/a | n/a |
| ABA 300 ppm | 1.75 | −5.6% | n/a |
| Malic acid 1000 ppm | 1.50 | −16.7% | n/a |
| ABA 300 ppm + Malic acid 1000 ppm | 2.15 | 22.2% | 1.6 |

"UTC" Denotes Untreated Control

As can be seen in Tables 11 and 12, ABA alone demonstrated evidence of increased fresh weight, whereas ABA alone demonstrated evidence of decreased dry weight and malic acid alone demonstrated evidence of decreased fresh and dry weight. A mixture of ABA and malic acid at a 1:3.3 ratio demonstrated an unexpected increase in both fresh weight and dry weight.

Example 9. Increased Photosynthesis Rate Under Drought Stress

Seven sets of corn plants (n=7) were each treated 16 DAP with either 300 or 1000 ppm ABA, 1000 ppm malic acid or mixtures thereof. Water was withheld from the date of chemical treatment. Photosynthesis rate was measured 1, 4 and 6 DAT. This experiment was repeated.

Results can be seen in Tables 13 and 14, below.

TABLE 13

| Experiment #1 | Photosynthesis Rate $CO_2$ assimilation (umol m$^{-2}$ s$^{-1}$) | | | % Change from UTC | | | OCE/ECE ratio | | |
|---|---|---|---|---|---|---|---|---|---|
| | 1 DAT | 4 DAT | 6 DAT | 1 DAT | 4 DAT | 6 DAT | 1 DAT | 4 DAT | 6 DAT |
| STC | 23.91 | 21.29 | 4.52 | 0.0% | 0.0% | 0.0% | n/a | n/a | n/a |
| 300 ppm ABA | 12.93 | 20.51 | 9.14 | −45.8% | −4.8% | 125.0% | n/a | n/a | n/a |
| 1000 ppm ABA | 9.23 | 19.05 | 19.15 | −62.5% | −14.3% | 375.0% | n/a | n/a | n/a |
| 1000 ppm Malic acid | 24.19 | 21.84 | 5.36 | 0.0% | 4.8% | 25.0% | n/a | n/a | n/a |
| 300 ppm ABA + 1000 ppm Malic acid | 14.73 | 22.48 | 11.38 | −41.7% | 9.5% | 200.0% | 1.1 | 1.1 | 1.2 |
| 1000 ppm ABA + 1000 ppm Malic acid | 7.74 | 16.51 | 15.03 | −70.8% | −23.8% | 275.0% | 0.8 | 0.8 | 0.8 |

TABLE 14

| Experiment #2 | Photosynthesis Rate | | | % Change from UTC | | | OCE/ECE ratio | | |
|---|---|---|---|---|---|---|---|---|---|
| | 1 DAT | 4 DAT | 6 DAT | 1 DAT | 4 DAT | 6 DAT | 1 DAT | 4 DAT | 6 DAT |
| STC | 22.78 | 19.83 | 9.99 | 0.0% | 0.0% | 0.0% | n/a | n/a | n/a |
| 300 ppm ABA | 18.23 | 20.06 | 9.21 | −17.4% | 0.0% | −10.0% | n/a | n/a | n/a |
| 1000 ppm ABA | 16.55 | 21.14 | 12.61 | −30.4% | 5.0% | 30.0% | n/a | n/a | n/a |
| 1000 ppm Malic acid | 21.97 | 21.05 | 8.09 | −4.3% | 5.0% | −20.0% | n/a | n/a | n/a |
| 300 ppm ABA + 1000 ppm Malic acid | 17.01 | 21.29 | 13.10 | −26.1% | 10.0% | 40.0% | 0.9 | 1.0 | 2.0 |
| 1000 ppm ABA + 1000 ppm Malic acid | 15.36 | 20.31 | 11.55 | −34.8% | 0.0% | 20.0% | 1.0 | 0.9 | 1.1 |

"UTC" denotes surfactant treated control

"UTC" Denotes Surfactant Treated Control

As can be seen in Tables 13 and 14, ABA alone demonstrated evidence of increased photosynthetic rate at 6 DAT and malic acid alone demonstrated evidence of both increased and decreased photosynthetic rates at 6 DAT. A mixture of ABA and malic acid at a 1:3.3 and a 1:1 ratio demonstrated an unexpected increase in photosynthetic rate at 6 DAT.

Example 10. Increased Yield of Rice Plants Under Not-Stressed Conditions and Drought Stressed Conditions A commercial semi-dwarf rice plant was used to test whether the combination of ABA and malic acid improves grain yield more than either alone. Rice was grown in the greenhouse using media composed of Profile Greens Grade in combination with ProMix®-BX in pots, which were saturated with water and fertilizer solutions. Treatments were applied to rice plants at early grain filling stage (5-20 days post-anthesis). Unexpected increases in grain yields were observed when the plants were treated with specific ratios of ABA and malic acid. See Tables 15-18, below. Yield is presented as panicle weight, where grain yield is about >95% of the panicle weight. The correlation between grain and panicle weights was >0.99. Individual applications of ABA (30 ppm) and malic acid (100 ppm) both decreased yield, while the mixture at a ratio of 1:3.3 unexpectedly increased yield by 8.2%. See Table 15, below.

TABLE 15

| Treatment and dose | Panicle Yield (g) | % Change from STC | OCE/ECE ratio |
|---|---|---|---|
| STC | 7.73 | n/a | n/a |
| ABA 30 ppm | 7.29 | −5.8% | n/a |
| Malic acid 100 ppm | 5.40 | −30.1% | n/a |
| ABA + Malic acid (30 + 100 ppm) | 8.36 | 8.2% | 1.7 |

The combination also unexpectedly improved rice yield at a ratio of 1:10 ABA (30 ppm) to malic acid (300 ppm). See Table 16 below. The mixture of ABA and malic acid resulted in 3.9% higher grain yield compared to the surfactant-treated control (STC).

TABLE 16

| Treatment and dose n = 6 | Panicle Yield | % Change from STC | OCE/ECE ratio |
|---|---|---|---|
| STC | 18.48 | n/a | n/a |
| ABA 30 ppm | 19.00 | 2.8% | n/a |
| Malic acid 300 ppm | 16.84 | −8.9% | n/a |
| ABA + Malic acid (30 + 300 ppm) | 19.20 | 3.9% | 1.1 |

In a similar study, rice plants were subjected to water deficit stress during early grain filling stages. The mixture of ABA (30 ppm) and malic acid (300 ppm) treated twice at around 10 and 17 days post-anthesis resulted in an unexpected increase in grain yield. See Table 17, below. The 1:10 ratio of ABA to malic acid mixture caused an unexpected increase in grain yield as compared to the compounds applied individually.

TABLE 17

| Treatment and dose n = 7 | Grain Yield (g) | % Change from STC | OCE/ECE ratio |
|---|---|---|---|
| STC | 11.56 | n/a | n/a |
| ABA 30 ppm | 11.88 | 2.7% | n/a |
| Malic acid 300 ppm | 10.58 | −8.5% | n/a |
| ABA + Malic acid (30 + 300 ppm) | 12.10 | 4.6% | 1.1 |

In another study, an ABA (30 ppm) and malic acid (1000 ppm) mixture at a ratio of 1:33.3 resulted in an unexpected increase in rice yield. See Table 18. The mixture showed a 7.8% increase in grain yield compared to the surfactant-treated control.

TABLE 18

| Treatment and dose n = 7 | Panicle Yield | % Change from STC | OCE/ECE ratio |
|---|---|---|---|
| STC | 16.50 | n/a | n/a |
| ABA 30 | 14.98 | −9.2% | n/a |
| Malic acid 1000 | 17.27 | 4.7% | n/a |
| ABA + Malic acid (30 + 1000 ppm) | 17.79 | 7.8% | 1.1 |

Stomatal conductance is a measure of the rate of gas exchange at the surface of a plant leaf. It is typically measured with a porometer using units of mmol $m^{-2}$ $s^{-1}$ vapor pressure. Following application of ABA to rice plants, stomatal conductance of the flag leaves of the main panicle, the first tiller and second tiller of seven plants of the milk stage in grain development of the main panicle were measured. We observed a reduction in leaf stomatal conductance within one day of application. See Table 19, below, demonstrating stomatal conductance (mmol m−2 s−1) of flag leaves of rice plants following foliar ABA application.

TABLE 19

| Treatment | One (1) day | Two (2) days |
|---|---|---|
| Treated Control | 277.4 | 286.0 |
| S-ABA, 10 ppm | 230.3 | 280.5 |
| S-ABA 30 ppm | 182.7 | 209.1 |

It is notable that the effect of ABA on stomatal conductance is short-lived, particularly at a low rate of ABA. The addition of malic acid to ABA significantly increased the effects of ABA or malic acid on rice flag leaf transpiration 24 h post-application. Table 20 shows the average of three separate studies examining the effects of ABA, malic acid or the mixtures on flag leaves of plants during grain fill. The data were also subjected to a calculation for OCE/ECE ratio.

TABLE 20

| Treatment | Transpiration at 1 day | % Change compared to Control | Expected | OCE/ECE ratio |
|---|---|---|---|---|
| Treated Control | 275.9 | 0.0% | | |
| ABA, 10 ppm | 277.6 | 0.6% | | |
| ABA, 30 ppm | 245.2 | −11.1% | | |
| Malic acid, 300 ppm | 255.8 | −7.3% | | |

TABLE 20-continued

| Treatment | Transpiration at 1 day | % Change compared to Control | Expected | OCE/ECE ratio |
|---|---|---|---|---|
| ABA 10 ppm + Malic acid, 300 ppm | 238.6 | −13.5% | −6.7% | 2.02 |
| ABA 30 ppm + Malic acid, 300 ppm | 228.5 | −17.2% | −18.4% | 0.93 |

The results clearly demonstrate that ABA and malic acid activity was unexpectedly increased by co-application at a ratio of 1:30 (ABA:malic acid). This reduction in stomatal conductance increases water banking and reduces stress caused by drought.

Example 11. Increased Yield in Wheat Plants Under Non-Stressed Conditions

A 10 feet by 50 feet plot were each treated at one week after anthesis with either 2 grams per hectare ("g/HA") ABA, 6 g/HA ABA, 20 g/HA, malic acid, 60 g/HA malic acid or a mixture thereof; chemical treatment with same compounds was repeated one week after initial spray. Plants were well-watered during entire period from planting to harvest. The plot was harvested to determine total yield except 3, 30 centimeter rows, which were harvested for detailed yield component analysis (above ground biomass ("AGB"), grain yield, harvest index, above ground moisture content ("AG Moisture"), number of heads, number of seeds per head, 1,000 seed weight and # of seeds. Results can be seen in Table 21, below.

TABLE 21

| | Yield (g/m$^2$) | AGB (g/m$^2$) | Grain Yield (g/m$^2$) | Harvest Index | AG Moisture (%) |
|---|---|---|---|---|---|
| STC | 379 | 1159 | 324 | 0.28 | 18.4 |
| ABA 2 g/HA | 372 | 1121 | 347 | 0.31 | 20.2 |
| ABA 6 g/HA | 383 | 1064 | 315 | 0.3 | 19.4 |
| Malic acid 60 g/HA | 369 | 1020 | 281 | 0.28 | 19.1 |
| ABA 2 g/HA + Malic acid 20 g/HA | 431 | 1256 | 432 | 0.35 | 21.2 |
| ABA 2 g/HA + Malic acid 60 g/HA | 415 | 1269 | 406 | 0.32 | 21.9 |
| OCE/ECE Ratio* | 1.1 | 1.4 | 1.5 | 1.1 | 1.1 |

| | # of heads/m$^2$ | # of seeds/head | 1,000 Seed Weight (grams) | # of seeds/m$^2$ |
|---|---|---|---|---|
| STC | 1041 | 14.3 | 22.3 | 14553 |
| ABA 2 g/HA | 1024 | 14.7 | 23.2 | 14909 |
| ABA 6 g/HA | 943 | 14.6 | 22.5 | 13817 |
| Malic acid 60 g/HA | 897 | 14.4 | 22.2 | 12748 |
| ABA 2 g/HA + Malic acid 20 g/HA | 953 | 19.23 | 23.9 | 18087 |
| ABA 2 g/HA + Malic acid 60 g/HA | 1087 | 15.7 | 22.5 | 17326 |
| OCE/ECE Ratio* | 1.4 | 1.1 | 1.0 | 1.4 |

"STC" denotes surfactant treated control
*based on percent change from STC

As can be seen in Table 21, a mixture of ABA and malic acid at a 1:30 ratio demonstrated an unexpected increase in yield, above ground biomass, grain yield, harvest index, above ground moisture content, heads per meter squared, seeds per head and seeds per meter squared.

What is claimed is:

1. A method of improving yield in a cereal grain crop comprising applying an effective amount of (S)-abscisic acid (ABA) and malic acid to the cereal grain crop, wherein the weight ratio of ABA to malic acid is from about 1:3.3 to about 1:33.3, wherein the cereal grain crop is subject to drought stressed conditions or not stressed conditions.

2. The method of claim 1, wherein the weight ratio of ABA to malic acid is from about 1:3.3 to about 1:10.

3. The method of claim 1 wherein the cereal grain crop is selected from the group consisting of corn, rice, and wheat.

* * * * *